United States Patent

Arcari et al.

[11] 3,996,228
[45] Dec. 7, 1976

[54] PYRIMIDINOAMINOETHYL ERGOLINE DERIVATIVES

[75] Inventors: Giuliana Arcari; Luigi Bernardi; Germano Bosisio; Alfredo Glasser; Aldemio Temperilli, all of Milan, Italy

[73] Assignee: Societa' Farmaceutici Italia S.p.A., Milan, Italy

[22] Filed: Dec. 9, 1974

[21] Appl. No.: 530,617

[30] Foreign Application Priority Data

Dec. 21, 1973 Italy .................. 54532/73

[52] U.S. Cl. .................. 260/256.4 C; 260/256.4 N; 260/256.5 R; 260/285.5; 424/251
[51] Int. Cl.[2] .................. C07D 457/02
[58] Field of Search ............ 260/256.4 N, 256.4 C, 260/285.5, 256.5 R

[56] References Cited

UNITED STATES PATENTS

| | | |
|---|---|---|
| 3,228,943 | 1/1966 | Bernardi et al. ............ 260/256.4 N |
| 3,238,099 | 3/1966 | Zimmermann ............ 260/256.4 N |
| 3,377,351 | 4/1968 | Haack et al. ............ 260/256.4 N |
| 3,499,898 | 3/1970 | von Bebenburg et al. ... 260/256.4 N |
| 3,646,046 | 2/1972 | Arcamone et al. ............ 260/285.5 |

OTHER PUBLICATIONS

Morrison et al.; *Organic Chemistry* 2nd Edition; (1969) p. 748.

Primary Examiner—Nicholas S. Rizzo
Assistant Examiner—Mary C. Vaughn
Attorney, Agent, or Firm—Hubbell, Cohen, Stiefel & Gross

[57] ABSTRACT

Pyrimidinoaminoethyl ergoline derivatives of the formula:

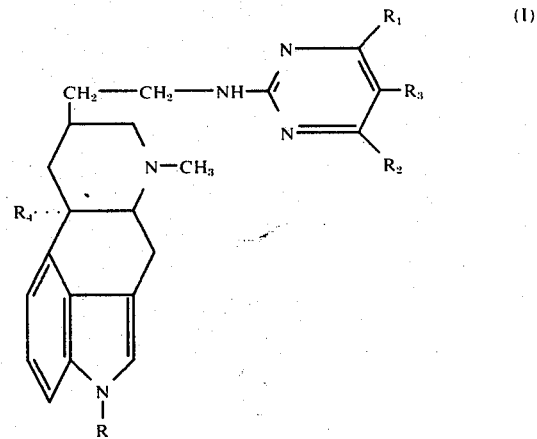

wherein R is hydrogen or methyl; $R_1$ and $R_2$ are independently selected from the group consisting of hydrogen, alkyl having 1 to 3 carbon atoms, methoxy and phenyl;

$R_3$ is hydrogen, halogen, alkyl and alkoxy each having 1 to 3 carbon atoms, phenyl, nitro, amino, cyano, acylamino, carboxamido and carbalkoxy each having 1 to 3 carbon atoms, trifluoromethyl or —$SO_2$—Y wherein Y is hydroxyl, amino or methyl and $R_4$ is hydrogen or methoxy are prepared by reacting an ergoline derivative of formula III and a 2-aminopyrimidine anion of formula II

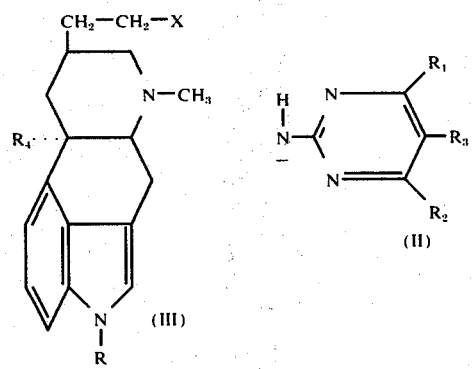

16 Claims, No Drawings

PYRIMIDINOAMINOETHYL ERGOLINE DERIVATIVES

BACKGROUND OF THE INVENTION

1. Field of the Invention

The invention relates to novel derivatives of ergoline and methods for their preparation.

2. Prior Art

Ergoline is a known compound.

SUMMARY OF THE INVENTION

According to the invention, there is provided a new class of ergoline derivatives, more specifically, a class of new pyrimidinoaminoethyl ergoline derivatives of the formula:

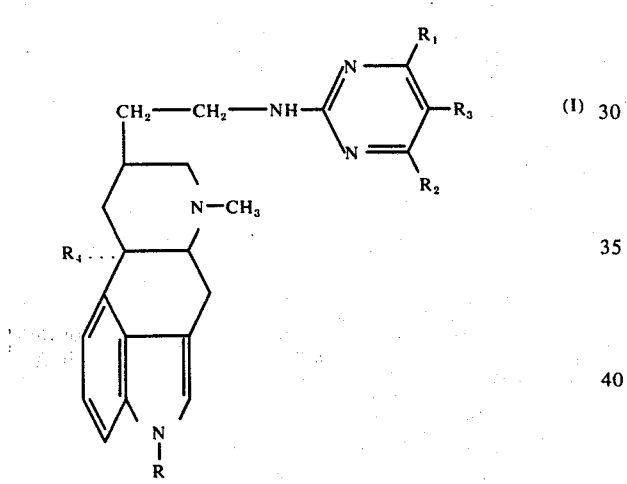

wherein R is hydrogen or methyl; $R_1$ and $R_2$ are independently selected from the group consisting of hydrogen, alkyl having 1 to 3 carbon atoms, methoxy and phenyl;

$R_3$ is hydrogen, halogen, alkyl and alkoxy each having 1 to 3 carbon atoms, phenyl, nitro, amino, cyano, acylamino, carboxamido and carbalkoxy each having 1 to 3 carbon atoms, trifluoromethyl or $-SO_2-Y$ wherein Y is hydroxyl, amino or methyl and $R_4$ is hydrogen or methoxy.

The invention further provides a new process for preparing the compound of formula I from an ergoline derivative of the formula III and a 2-aminopyrimidine anion of the formula II according to the following scheme:

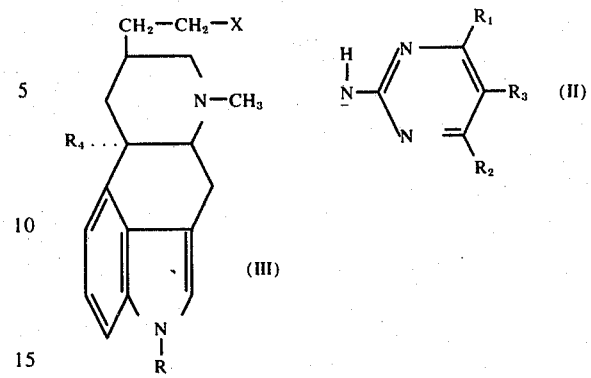

wherein R, $R_1$, $R_2$, $R_3$, and $R_4$ are as defined above and X is chlorine, bromine, mesyl or tosyl.

The pyrimidine anion (II) is prepared directly in the reaction mixture according to the scheme:

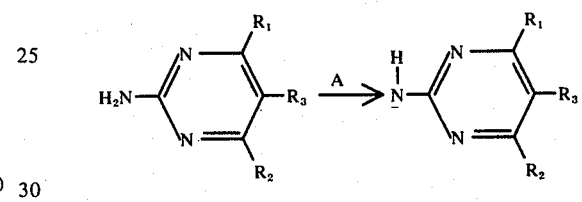

wherein A is a strong base such as butyllythium, sodium amide, potassium amide, sodium hydride or potassium hydride and it is selected according to the nature of the group attached to position 5 of the pyrimidino ring.

Thus, if the substituent in the 5-position is an electron-attracting group such as nitro or cyano, the hydrides are preferred; if the substituent in the 5-position is an electron donor such as methyl, sodium or potassium amide is preferred.

The reaction is carried out in a suitable solvent such as dimethylformamide. The ergoline derivative of formula III, dissolved in the same solvent that is employed for the preparation of the pyrimidino anion is then added. The reaction mixture is heated to a temperature of 50° to 110° C, for 30 minutes to 5 hours.

When the reaction is complete, the solvent is evaporated off, the residue is dissolved and then filtered, after which the obtained compound is purified by crystallization or chromatography according to well-known techniques.

The compounds of the present invention have a high and prolonged adrenolytic activity and a low toxicity and are therefore useful in therapy. This adrenolytic activity was tested "in vitro" on isolated guinea pig seminal vescicle suspended in physiological solution and "in vivo" on the rat. Table 1 reports the values of concentrations, in $\gamma$/ml, which are able to produce a 50% inhibition ($IC_{50}$) of the spasmogen effect caused by adrenaline and the doses in mg/Kg ($ED_{50}$) able to reduce by 50% the lethal effects caused by adrenaline after oral (os) and intravenous (i.v.) administration of the compounds in question. Table 1 also reports the $LD_{50}$ values, both per os and i.v. in rats.

Table I

| Compound | Adrenolytic Activity | | | LD $_{50}$mg/Kg | |
|---|---|---|---|---|---|
| | "in vitro" IC $_{50}$γ/ml | "in vivo" ED $_{50}$mg/kg i.v. | ED $_{50}$mg/Kg os | i.v. | os |
| 1,6-Dimethyl-8 β[5-nitro-2-pyrimidino-aminoethyl]-10α-methoxyergoline | 0.5 | 0.25 | 0.42 | — | 150 |
| 1,6-Dimethyl-8β-[2-pyrimidinoaminoethyl]-10α-ergoline | 0.001 | 0.2 | 0.1 | 18 | 100 |
| 1,6-Dimethyl-8β-[5-bromo-2-pyrimidino-aminoethyl]-10α-methoxyergoline | 0.01 | 0.65 | >1 | — | 200 |
| 1,6-Dimethyl-8β-[5-methyl-2-pyrimidino-aminoethyl]-10α-ergoline | 0.5 | 0.07 | 0.5 | 19 | 130 |

In addition, it has also been found that some of the compounds according to the invention display an unexpected hypotensive, analgesic, antiserotonin and sedative activity. The hypotensive and analgesic data for some of the compounds are given in Table II.

The hypotensive activity was tested on the hypertensive rat; the reported data being the dose expressed in mg/Kg per os, which causes a pressure drop of about 30–40 mmHg.

The analgesic activity was evaluated by means of the hot plate test and the writhing test, the data being given in comparison with morphine and D-propoxyphene.

Table II

| Compound | Hypotensive Activity active dose mg/Kg - os | Analgesic Activity | | | |
|---|---|---|---|---|---|
| | | Hot Plate | | Writhing | |
| | | morphine | D.propoxyphene | morphine | D.propoxyphene |
| 1,6-Dimethyl-8β-[5-amino-2-pyrimidino-aminoethyl]-10α-ergoline | 10 | 1 | 5 | 1 | 10 |
| 1,6-Dimethyl-8β-[5-methoxy-2-pyrimidino-aminoethyl]-10α-ergoline | 10 | 0.5 | 2 | — | — |

In the hot plate and writhing tests, the comparison compounds morphine and D-propoxyphene have been arbitrarily assigned the value of 1. Thus, in the hot plate test, the compound 1,6-dimethyl-8β-[5-amino-2-pyrimidino-aminoethyl]-10α-ergoline has the same activity as morphine and 5 times the activity of D-propoxyphene, while in the writhing test, it has the same activity as morphine and 10 times the activity of D-propoxyphene.

DESCRIPTION OF THE PREFERRED EMBODIMENTS

The following examples illustrate the invention without limiting the scope thereof.

EXAMPLE 1

1,6-Dimethyl-8β-[5-nitro-2-pyrimidinoaminoethyl]-10α-methoxyergoline 0.6 g of 2-amino-5-nitropyrimidine are added, with shaking, and under a nitrogen atmosphere to 0.17 g of sodium hydride (50% dispersion in mineral oil) suspended in 20 cc of dimethylformamide. When the evolution of hydrogen is complete, 1.5 g of 1,6-dimethyl-8β-chloroethyl-10α-methoxyergoline, dissolved in 12 cc of dimethylformamide are added, and the solution is heated at 100° C for 4 hours. The dimethylformamide is evaporated off and the mineral oil is removed by treatment with n-pentane. The residue is dissolved in boiling ethyl ether and filtered while warm. After evaporation of the ether, the residue is crystallized from acetone and 0.420 g of the product, melting at 216°–218° C are obtained.

EXAMPLE 2

1,6-Dimethyl-8β-[5-methyl-2-pyrimidinoaminoethyl]-10α-ergoline

To a solution of 0.085 g of sodium amide in 100 cc of liquid ammonia, 0.237 g of 2-amino-5-methylpyrimidine are added with shaking. The ammonia is slowly evaporated off and 0.55 g of 1,6-dimethyl-8β-chloroethyl-10α-ergoline in 40 cc of anhydrous dimethylsulfoxide are added. The solution is heated, with shaking, at 60° C for 30 minutes after which the dimethylsulfoxide is evaporated and the residue is dissolved in water and chloroform. The chloroform solution is evaporated and the residue is chromatographed on aluminium oxide using chloroform as a solvent. 0.205 g of the product melting at 140°–142° C are collected.

EXAMPLE 3

1,6-Dimethyl-8β-[5-bromo-2-pyrimidinoamino-ethyl]-10α-methoxyergoline

By operating as described in Example 1, but using 2-amino-5-bromopyrimidine, there is obtained 1,6-dimethyl-8β-[5-bromo-2-pyrimidinoaminoethyl]-10α-methoxyergoline melting at 145°–147° C.

EXAMPLE 4

1,6-Dimethyl-8β-[5-bromo-2-pyrimidinoaminoethyl]-10α-ergoline

By operating as described in Example 1, but using 2-amino-5-bromopyrimidine and 1,6-dimethyl-8β-chloroethyl-10α-ergoline, there is obtained 1,6-dimethyl-8β-[5-bromo-2-pyrimidinoaminoethyl]-10α-ergoline melting at 131°–133° C.

EXAMPLE 5

1,6-Dimethyl-8β-[2-pyrimidinoaminoethyl]-10α-methoxyergoline

By operating as described in Example 2, but using 2-aminopyrimidine, there is obtained 1,6-dimethyl-8β-[2-pyrimidinoaminoethyl]-10α-methoxyergoline melting at 162°–164° C.

EXAMPLE 6

1,6-Dimethyl-8β-[5-methoxy-2-pyrimidinoaminoethyl]-10α-methoxyergoline

By operating as described in Example 2, but using 2-amino-5-methoxy-pyrimidine and 1,6-dimethyl-8β-chloroethyl-10α-methoxyergoline, there is obtained 1,6-dimethyl-8β-[5-methoxy-2-pyrimidinoaminoethyl]-10α-methoxyergoline melting at 105°–107° C.

EXAMPLE 7

1,6-Dimethyl-8β-[5-cyano-2-pyrimidinoaminoethyl]-10α-methoxyergoline

By operating as described in Example 1, but using 2-amino-5-cyano-pyrimidine, there is obtained 1,6-dimethyl-8β-[5-cyano-2-pyrimidinoaminoethyl]-10α-methoxyergoline melting at 223°–225° C.

EXAMPLE 8

By operating as described in Example 1, but using 1,6-dimethyl-8β-chloroethyl-10α-ergoline and a suitably 5-substituted-2-aminopyrimidine, the following compounds are obtained:

1,6-dimethyl-8β-[5-nitro-2-pyrimidinoaminoethyl]-10 α-ergoline; melting point 195°–197° C;

1,6-dimethyl-8β-[5-cyano-2-pyrimidinoaminoethyl]-10α-ergoline; melting point 148°–150°C;

1,6-dimethyl-8β-[5-carbethoxy-2-pyrimidinoaminoethyl]-10α-ergoline; melting point 143°–145° C.

By operating as described in Example 2, and using a suitable 2-amino-pyrimidine and 1,6-dimethyl-8β-chloroethyl-10α-ergoline, the following compounds are obtained:

1,6-dimethyl-8β-[5-phenyl-2-pyrimidinoaminoethyl]-10α-ergoline; melting point 175°–177° C;

1,6-dimethyl-8β-[2-pyrimidinoaminoethyl]-10α-ergoline; melting point 130°–132° C;

1,6-dimethyl-8β-[5-methoxy-2-pyrimidinoaminoethyl]-10α-ergoline; melting point 126°–128° C.

Furthermore, by hydrogenation of 1,6-dimethyl-8β-[5-nitro-2-pyrimidino-aminoethyl]-10α-ergoline in ethanol in the presence of 5% Pd/Al₂O₃ at room temperature and atmospheric pressure, the 5-amino derivative, i.e., 1,6-dimethyl-8β-[5-amino-2-pyrimidinoaminoethyl]-10α-ergoline; melting at 168°–170° C was obtained. Acetylation of the amino compound with acetic anhydride in refluxing benzene for 2 hours yields the 5-acetylamino derivative, i.e., 1,6-dimethyl-8β-[5-acetyl-amino-2-pyrimidinoaminoethyl]-10α-ergoline melting at 214°–216° C.

EXAMPLE 9

This example described a pharmaceutical composition comprising a compound according to the invention and intended for oral administration

| active component (compound according to the invention) | 2 | mg |
|---|---|---|
| calcium phosphate | 100 | mg |
| sodium carboxymethylcellulose | 1.3 | mg |
| magnesium stearate | 1.3 | mg |
| microcrystalline cellulose | 22.4 | mg |

Tablets formed from the foregoing composition are orally administered in a dosage of from 1 to 5 tablets per day. This corresponds to a dosage of 2–10 mg/per day of active compound.

EXAMPLE 10

This example described a pharmaceutical composition comprising a compound according to the invention and intended for parenteral administration

| active component (compound according to the invention) | 0.4 | mg |
|---|---|---|
| tartaric acid | 1 | mg |
| mannitol | 100 | mg |
| pyrogen free water | 2 | mg |

This composition is administered parenterally in a dosage of 1 to 10 ml per day.

Variations can, of course, be made without departing from the spirit and scope of the invention.

Having thus described our invention, what we desire to secure by Letters Patent and hereby claim is:

1. A compound having the formula:

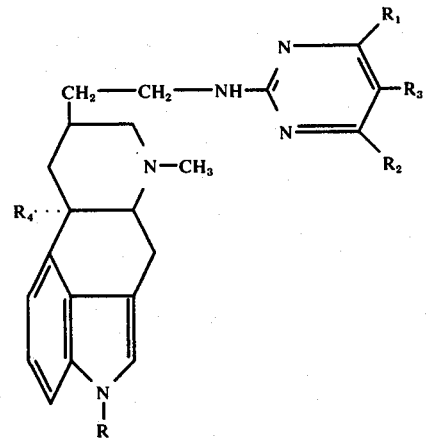

wherein R is hydrogen or methyl; R₁ and R₂ are independently selected from the group consisting of hydrogen, alkyl having 1 to 3 carbon atoms, methoxy and phenyl; R₃ is hydrogen, halogen, alkyl having 1 to 3 carbon atoms, alkoxy having 1 to 3 carbon atoms, phenyl, cyano, nitro, amino, acylamino, wherein the acid residue is derived from a monocarboxylic acid having 1 to 3 carbon atoms, carboxamido having 1 to 3 carbon atoms, carbalkoxy having 2 to 4 carbon atoms, trifluoromethyl or —SO₂—Y wherein Y is hydroxyl, amino or methyl; and R₄ is hydrogen or methoxy.

2. The compound of claim 1, which is 1,6-Dimethyl-8β-[5-nitro-2-pyrimidinoaminoethyl]-10α-methoxyergoline.

3. The compound of claim 1, which is 1,6-Dimethyl-8β-[5-methyl-2-pyrimidinoaminoethyl]-10α-ergoline.

4. The compound of claim 1, which is 1,6-Dimethyl-8β-[5-bromo-2-pyrimidinoaminoethyl]-10α-methoxyergoline.

5. The compound of claim 1, which is 1,6-Dimethyl-8β-[5-bromo-2-pyrimidinoaminoethyl]-10α-ergoline.

6. The compound of claim 1, which is 1,6-Dimethyl-8β-[2-pyrimidinoaminoethyl]-10α-methoxyergoline.

7. The compound of claim 1, which is 1,6-Dimethyl-8β-[5-methoxy-2-pyrimidinoaminoethyl]-10α-methoxyergoline.

8. The compound of claim 1, which is 1,6-Dimethyl-8β-[5-cyano-2-pyrimidinoaminoethyl]-10α-methoxyergoline.

9. The compound of claim 1, which is 1,6-Dimethyl-8β-[5-nitro-2-pyrimidinoaminoethyl]-10α-ergoline.

10. The compound of claim 1, which is 1,6-Dimethyl-8β-[5-cyano-2-pyrimidinoaminoethyl]-10α-ergoline.

11. The compound of claim 1, which is 1,6-Dimethyl-8β-[5-carbethoxy-2-pyrimidinoaminoethyl]-10α-ergoline.

12. The compound of claim 1, which is 1,6-Dimethyl-8β-[5-phenyl-2-pyrimidinoaminoethyl]-10α-ergoline.

13. The compound of claim 1, which is 1,6-Dimethyl-8β-[2-pyrimidinoaminoethyl]-10α-ergoline.

14. The compound of claim 1, which is 1,6-Dimethyl-8β-[5-methoxy-2-pyrimidinoaminoethyl]-10α-ergoline.

15. The compound of claim 1, which is 1,6-Dimethyl-8β-[5-amino-2-pyrimidinoaminoethyl]-10α-ergoline.

16. The compound of claim 1, which is 1,6-Dimethyl-8β-[5-acetylamino-2-pyrimidinoaminoethyl]-10α-ergoline.

UNITED STATES PATENT OFFICE
CERTIFICATE OF CORRECTION

Patent No. 3,996,228                     Dated December 7, 1976

Inventor(s) GIULIANA ARCARI et al

It is certified that error appears in the above-identified patent and that said Letters Patent are hereby corrected as shown below:

Title page, right side, formula (II):

" 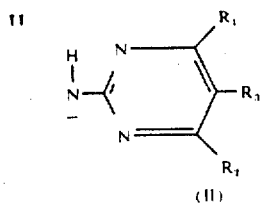 " should read -- 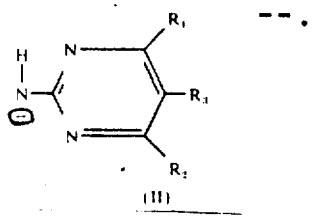 --.

Column 2, lines 1-6, formula (II):

" 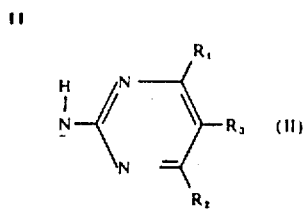 " should read -- 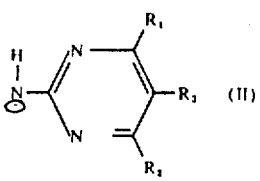 --.

Column 2, lines 25-20:

" 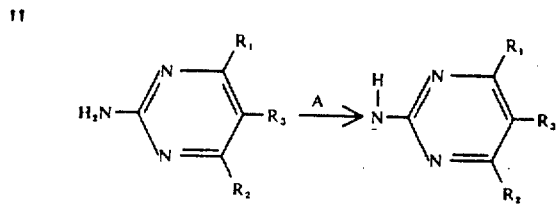 " should read

UNITED STATES PATENT OFFICE
CERTIFICATE OF CORRECTION

Patent No. 3,996,228   Dated December 7, 1976

Inventor(s) GIULIANA ARCARI et al

It is certified that error appears in the above-identified patent and that said Letters Patent are hereby corrected as shown below:

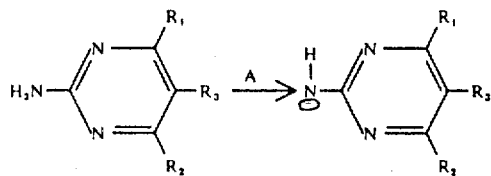

Column 5, line 54: "described" should read -- describes --.

Column 6, line 1: "described" should read -- describes --.

Signed and Sealed this

Eighth Day of February 1977

[SEAL]

Attest:

RUTH C. MASON  
*Attesting Officer*

C. MARSHALL DANN  
*Commissioner of Patents and Trademarks*